United States Patent [19]

Fulwyler

[11] 4,230,558
[45] Oct. 28, 1980

[54] SINGLE DROP SEPARATOR

[75] Inventor: Mack J. Fulwyler, Los Alamos, N. Mex.

[73] Assignee: Coulter Electronics, Inc., Hialeah, Fla.

[21] Appl. No.: 947,853

[22] Filed: Oct. 2, 1978

Related U.S. Application Data

[63] Continuation of Ser. No. 843,696, Oct. 19, 1977, Pat. No. 4,148,718, which is a continuation of Ser. No. 694,532, Jun. 10, 1976, abandoned.

[51] Int. Cl.³ .............................................. B07C 5/34
[52] U.S. Cl. ..................................... 209/3.1; 209/579; 209/932
[58] Field of Search ................... 209/3, 11, 3.1, 127 R, 209/3.2, 127 A, 127 C, 571, 579, 906, 638; 239/3, 15, 101; 346/75, 1

[56] References Cited

U.S. PATENT DOCUMENTS

| | | | |
|---|---|---|---|
| 3,380,584 | 4/1968 | Fulwyler | 209/127 R X |
| 3,596,275 | 7/1971 | Sweet | 346/75 X |
| 3,826,364 | 7/1974 | Bonner et al. | 209/3.1 |
| 3,878,519 | 4/1975 | Eaton | 346/1 |
| 3,979,756 | 9/1976 | Helinski et al. | 346/75 X |

OTHER PUBLICATIONS

Fulwyler et al., Review of Scientific Instruments, vol. 40, No. 1, Jan. 1969, pp. 42–48.

*Primary Examiner*—Ralph J. Hill
*Attorney, Agent, or Firm*—Silverman, Cass & Singer, Ltd.

[57] ABSTRACT

A method and apparatus for forming a separate single drop wherein a fluid stream is formed in air and an electrical charge or radiant energy is applied to the stream at a particular location in order to disturb the stream and create a single drop. The drop may be formed surrounding a particle and the drop may be charged when formed, then deflected for separate collection.

6 Claims, 3 Drawing Figures

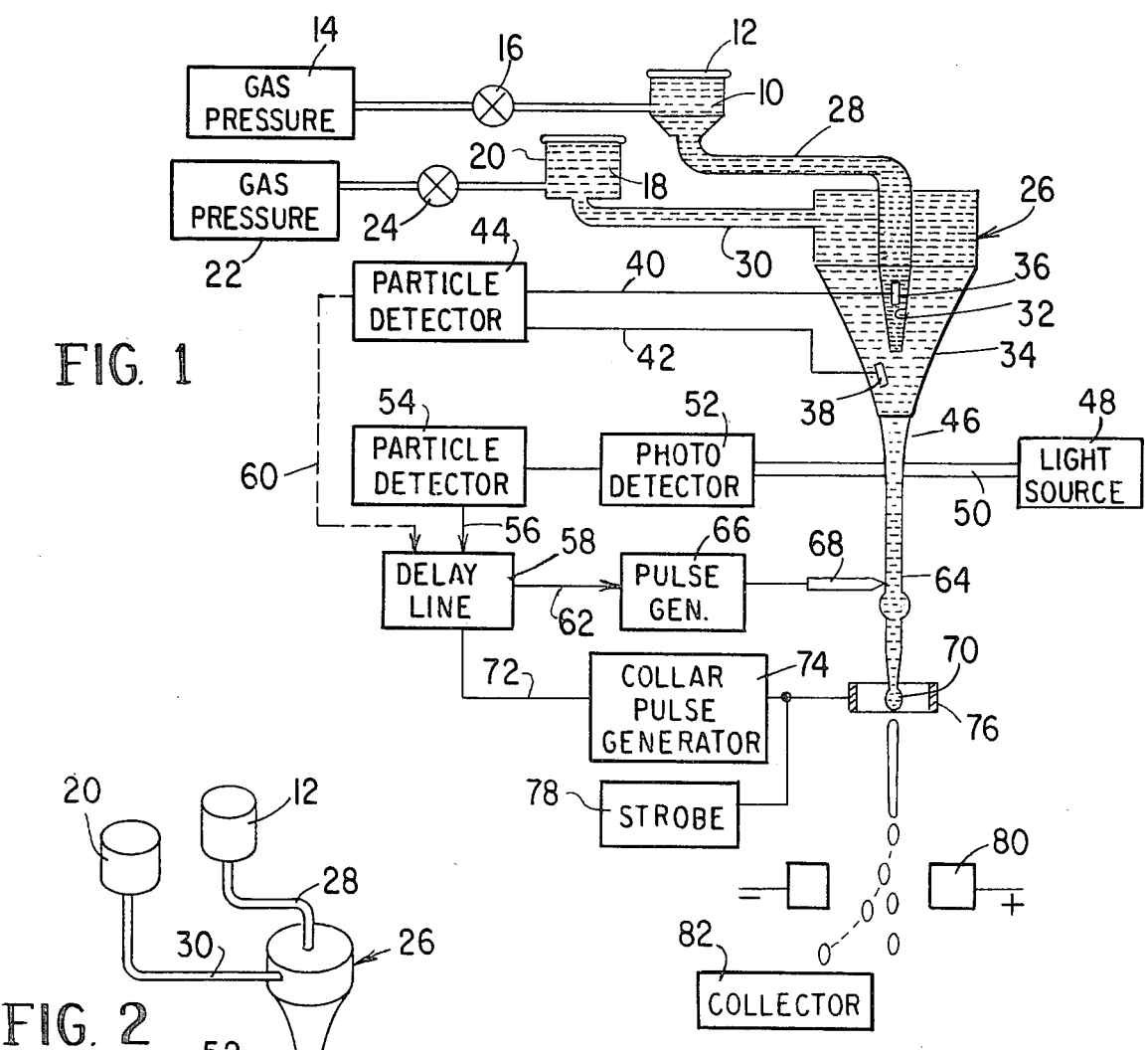
FIG. 1
FIG. 2
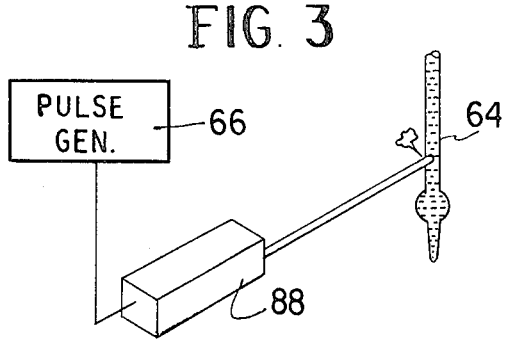
FIG. 3

SINGLE DROP SEPARATOR

This is a continuation, of application Ser. No. 843,696, filed Oct. 19, 1977, now U.S. Pat. No. 4,148,718, issued Apr. 10, 1979, which is a continuation of application Ser. No. 694,532, filed June 10, 1976, now abandoned.

BACKGROUND OF THE INVENTION

This invention relates to an apparatus and method for separately forming single drops from a fluid suspension and more particularly relates to a method and apparatus for detecting a particle in a fluid stream forming the particle in a droplet and separating that droplet from the fluid stream.

An apparatus capable of sorting minute particles in accordance with distinctive characteristics among the particles themselves has many important uses. For example, in the field of biology, it would be useful to sort blood cells in accordance with size. U.S. Pat. No. 3,380,584 issued to Mack J. Fulwyler, the applicant herein, shows and describes a method and apparatus for detecting and separating particles such as blood cells. The apparatus shown in the above-noted patent includes an orifice through which fluid containing the particles is caused to flow. The fluid is vibrated or pulsed by an accoustical device causing the fluid to jet through the orifice and form a fluid stream in air which separates into discrete equal volume droplets. As the particles pass through the orifice they are sensed, and as the droplet surrounding each particle is formed, it is charged so that the droplet and particle can be deflected for collection.

Although the above noted apparatus has allowed particle detection and separation at a rate, and in a manner previously considered impossible, certain problems have arisen.

In the apparatus described in the above noted patent, the acoustical device takes the form of a piezoelectric generator that vibrates at a 40 KHz rate. The vibrations are periodic, however, the particles passing through the apparatus are detected at random intervals. Because the pulsing is periodic and the detection is random, there is no assurance that each detected particle will be enclosed in a formed droplet. It is possible that a particle will appear at the neck between formation of two droplets. For this reason, it is necessary to charge and deflect at least two particles in series in order to ensure collection of the detected particle.

The above noted apparatus envisions the possibility of two different types of particle detection. One type of particle detection employs a laser beam which passes through the fluid stream, jetted into air, to a photodetector. As the particle passes through the laser beam, the change in laser light coupled to the photodetector is sensed thus recognizing a particle passage. For this type of detection to be feasible, the fluid surrounding the particle must move uniformly with as few disturbances as possible so that the laser beam is not disturbed in its passage to the photodetector. The 40 KHz vibration produced by the acoustical driver creates tiny disturbances on the fluid stream which are undesirable and should be eliminated to minimize disturbance of the laser beam.

The other type of detection employs two electrodes, one on either side of an aperture, and in contact with the particle laden fluid. The electrical resistance between the electrodes is affected by the presence and size of a particle passing through the aperture and this change in resistance is detected. This type of detection is somewhat sensitive to extraneous noise and the 40 kHz periodic vibrations produced by the piezoelectric generator constitutes a source of noise which can affect the detector operation.

SUMMARY OF THE INVENTION

In practicing this invention there is provided a method for forming and separating a drop in a fluid stream. The method includes forming the fluid stream itself, discharging the fluid stream into air in a continuous flow, and applying one of an electrical charge or radiant energy to the fluid stream in air at a particular location in the continuous flow to distrub the stream and create a single drop.

The apparatus for practicing the above noted method includes structure for forming a fluid stream and for discharging the stream into air and an application device in communication with the stream in air at a first location which operates to apply one of the electrical charge or radiant energy to the stream for disturbing the stream and creating the drop.

BRIEF DESCRIPTION OF THE DRAWINGS

FIG. 1 is a block diagram of the apparatus of the present invention;

FIG. 2 is a perspective view of part of the apparatus shown in FIG. 1;

FIG. 3 is a perspective and block diagram view of a portion of an alternate embodiment of this invention.

DETAILED DESCRIPTION OF THE PREFERRED EMBODIMENT

Referring to the figures, liquid 10 containing particles in suspension which are to be detected, is stored in a suitable container 12. The liquid is maintained under pressure from a gas pressure source 14 and pressure regulator 16. A particle free sheath fluid 18 is stored in a container 20 and is maintained under pressure by gas pressure source 22 and pressure regulator 24. Liquid 10 and particle free sheath fluid 18 are connected to a nozzle assembly 26 by way of conduits 28 and 30 respectively.

Nozzle assembly 26 includes inner and outer coaxially located nozzles 32 and 34 which are supplied with liquid 10 and fluid 18 through conduits 28 and 30 respectively. An electrode 36 is positioned interior to nozzle 32, and a second electrode 38 is positioned interior to nozzle 34 and exterior to nozzle 32. Electrodes 36 and 38 are connected by way of conductors 40 and 42 respectively to a particle detector 44.

The structure is such that liquid 10 is ejected from the orifice at the end of nozzle 32 into the center of a flowing stream of sheath fluid 18 interior to nozzle 34. The particle laden liquid 10 surrounded by sheath fluid 18 exits through the aperture in outer nozzle 34 as a continuous coaxial fluid flow stream 46 having a diameter of approximately 70 microns. The inner stream portion containing the particles is reduced in diameter to approximately 15 microns.

Particles passing through inner nozzle 32 will cause a change in electrical resistance between electrodes 36 and 38 which change is sensed by particle detector 44. Particle detector 44 may include means for sizing the detected particle and further may include means for recording the detection and size information. A detection signal may be provided by detector 44.

Sensing of the particles in the fluid stream 46 outside of the nozzle may also be provided and this is accomplished by a laser light source 48 which projects a laser beam 50 through the continuous fluid flow stream 46 at a first location to a photodetector 52. The passage of a particle in flow stream 46 through beam 50 will affect the light pattern received by photodetector 52. The change in light pattern at photodetector 52 is detected by particle detector 54 in order to size and identify the detected particle. Particle detector 54 may also include means for recording the particle detection information.

Assume for this discussion that a particle passing through nozzle assembly 26 is first detected by particle detector 44 and then by particle detector 54. Particle detector 54 will develop a detection signal which is coupled by way of conductor 56 to delay line 58. It should be understood that the detection signal developed by particle detector 44 also may be coupled to delay line 58. Such a connection is shown by way of dashed line 60. Delay line 58 will develop a delay signal a predetermined period of time after receipt of the detection signal from particle detector 54 or 44. The delay period may be adjusted by means of internal adjustment apparatus in delay line 58 and is selected such that delay line 58 will develop a first delay signal at conductor 62 when the detected particle is present at a second location 64 downstream of the first location in the continuous fluid flow stream 46. The delay signal developed at conductor 62 is coupled to a pulse generator 66 which develops a positive voltage pulse that is coupled to electrode 68. Electrode 68 is positioned at second location 64 and is positioned very close to the continuous fluid flow stream 46 so that the pulse developed by pulse generator 66 is coupled to stream 46 by way of electrode 68.

It has been found that the application of a pulse having certain characteristics to a continuous fluid flow stream will charge the stream at the location of application. This charge acts as a disturbance on the stream and will result in the somewhat gradual growth of a drop in the stream at the charge application location. If the charge is properly applied, the drop will form at a location downstream of second location 64 and will form by first separating from the continuous fluid flow stream portion preceding the drop downstream and then separate from the continuous fluid flow stream portion following the drop.

The exact reasons for the formation of a drop in response to application of a charge are at this time obscure. Lord Raleigh found that the primary effect which holds a drop together is surface tension. If a positive charge is applied to a drop and the drop is allowed to evaporate so that the charges more closely approach one another, a point will be reached where the repulsive forces on the drop produced by the positive charge will offset the drop surface tension and the drop will disintegrate. It is therefore believed that the application of charge to the flow stream creates a repulsive force which offsets the surface tension in the fluid stream itself and allows a single uniform drop to form at the point of charge application.

As mentioned previously, it is most desirable to have the drop form in two stages. The first stage requires that the drop pinch off from the fluid stream preceding the drop downstream and the second stage is separation of the drop from the fluid flow stream following the drop.

In order to form the drop itself it has been found necessary to apply a charging pulse having a particular amplitude and duration. It has been found that pulses having an amplitude of 50 to 400 volts and durations of 5 to 50 microseconds are effective to form drops when the flow stream has an initial diameter of approximately 70 microns. Pulses having an amplitude of 200 volts and duration of 50 microseconds have been found most effective. It is also believed that a varying amplitude pulse having a higher initial voltage than terminal voltage is most effective in causing the desired two stage drop separation from the continuous flow stream. For example, the desired pulse should rise abruptly from zero to 200 volts, then slowly decrease in amplitude to approximately 100 volts at the end of a 50 microsecond interval, then abruptly drop from 100 volts to zero volts at 50 microseconds. With a pulse formed such as described and applied to the continuous fluid flow stream 46, a drop should form in two stages as noted. In the embodiment shown and with a known and constantly maintained fluid flow rate for continuous fluid flow stream 46 the droplet will be formed at a third location 70.

In the embodiment described, the charge pulse applied by electrode 68 at location 64 was applied to the fluid stream when the detected particle passed through second location 64. As the fluid flow stream 46 surrounding the droplet was charged at second location 64, the detected particle will be contained in the single drop formed at third location 70. Delay line 58, in addition to developing a first delay signal at conductor 62, also is operative to develop a second delay signal at conductor 72. Again, as with the delay signal developed at conductor 62 the delay signal developed at conductor 72 can be adjusted to occur at any desired period after the detection signal from particle detector 54 by way of delay adjustment means internal to delay line 58. The second delay signal is coupled by conductor 72 to a collar pulse generator 74 which operates in response to the received second delay signal to develop a positive charging pulse which is applied to charging collar 76 and to a strobe 78. The charge is applied to charging collar 76 just as the drop containing the detected particle is formed and as it is about to pinch off from the fluid flow stream 46 which follows the drop. Charging the drop prior to pinch off from stream 46 is necessary to assure application of the full charge to the drop itself. Strobe unit 78 is directed at location 70 in order to freeze motion thereat so as to allow determination of the tme when the above described pinch off occurs. The adjustment means in delay line 58 is used in conjunction with strobe 78 in order to fix the point in time at which the charge is applied to charging collar 76.

The charged drop containing the particle, separated from the preceding and succeeding flow stream, proceeds downstream and passes through a deflection plate 80. The positively charged drop is repulsed by one charging plate and attracted by the other causing the drop to deflect from the downward vertical path to a collector 82 where the particle may be collected and stored for later evaluation.

In an alternate embodiment a heater element may be provided in place of electrode 68. For purposes of this explanation the heater element will be identified in FIGS. 1 and 2 by the number 68.

In this embodiment, the positive voltage pulse developed by pulse generator 66 is coupled to heater 68 causing the heater to instantaneously heat and couple the developed radiant energy to the adjacent continuous fluid flow stream 46. The application of radiant energy in the form of heat is based upon a principle somewhat similar to the principle discussed above for application of electrical charge. Here, however, the surface tension of the fluid flow stream is affected by the heat which in turn causes formation of a drop.

A preferred method of application of radiant energy is illustrated partially in FIG. 3. FIG. 3 shows the fluid stream 46 and pulse generator 66. The output of pulse generator 66 in this embodiment is coupled to a high intensity, high energy laser 88. The remaining apparatus is identical to that shown in FIGS. 1 and 2 and need not be discussed in detail.

The voltage pulse developed by pulse generator 66 and coupled to laser 88 causes laser 88 to develop a high intensity, high energy laser beam that is directed into fluid stream 46 at location 64. The high intensity, high energy beam instantaneously heats the stream at location 64. This heating causes a variation in the stream surface tension which results in the formation of a single drop.

While the present invention has been described by reference to a specific apparatus, it is to be understood that modifications may be made by those skilled in the art without actually departing from the invention shown and described herein. It is therefore intended that the appended claims cover all variations that fall within the scope and spirit of this invention.

What is desired to be secured by Letters Patent of the United States is:

1. An apparatus for detecting and selectively separating small particles in a fluid including in combination:

forming means for forming a moving fluid stream in air having a substantially constant velocity containing said particles asynchronously spaced in said stream, sensing means adjacent said fluid stream and operative to detect a particle in said stream passing a first location and to develop a detection signal, pulse generation means coupled to said sensing means and communicating with said fluid stream at a second location, said pulse generation means operative in response to said detection signal to apply one of an electrical pulse and a quantum of radiant energy to said stream and particle therein at said second location for asynchronously disturbing said stream and creating a single isolated droplet from said stream surrounding said particle separated from the preceding and succeeding fluid stream.

2. The apparatus of claim 1 wherein said pulse generation means includes charging means for applying said electrical pulse to said fluid stream.

3. The apparatus of claim 1 wherein said pulse generation means include light generation means for developing a high intensity light beam, said high intensity light beam developing substantial radiant energy for application to said fluid stream.

4. The apparatus of claim 1 wherein said pulse generation means include heating means for developing said radiant energy and applying same to said fluid stream.

5. The apparatus of claim 1 wherein said droplet is created by separation from said fluid stream at a third location and further including second pulse generation means coupled to said sensing means and communicating with said stream at said third location, said second pulse generation means operative in response to said detection signal to apply a second electrical pulse to said stream and particle therein as said droplet separates from said stream for charging said droplet, and deflection means for deflecting said charged droplet to a collection device.

6. The apparatus of claim 5 including delay means coupling said sensing means to said first and second pulse generators, said delay means operative in response to said detection signal to develop a first and second delay signal, said pulse generation means operative in response to said first delay signal to develop said electrical pulse, said second pulse generation means operative in response to said second delay signal to develop said second electrical pulse.

* * * * *